United States Patent [19]

Dietschi

[11] Patent Number: 4,919,675

[45] Date of Patent: Apr. 24, 1990

[54] HEMISPHERICAL PROSTHETIC ACETABULUM

[75] Inventor: Carlo Dietschi, Lugano, Switzerland

[73] Assignee: Sulzer Brothers Limited, Winterthur, Switzerland

[21] Appl. No.: 315,560

[22] Filed: Feb. 23, 1989

[30] Foreign Application Priority Data

Feb. 26, 1988 [CH] Switzerland ............................. 718/88

[51] Int. Cl.$^5$ ................................................ A61F 2/34
[52] U.S. Cl. ........................................................ 623/22
[58] Field of Search ............................ 623/16, 18, 22, 23

[56] References Cited

U.S. PATENT DOCUMENTS

| 4,031,570 | 6/1977 | Frey | 623/22 |
| 4,624,674 | 11/1986 | Pappas et al. | 623/22 |
| 4,714,477 | 12/1987 | Fichera et al. | 623/22 |

FOREIGN PATENT DOCUMENTS

| 0226762 | 7/1987 | European Pat. Off. | |
| 0265712 | 5/1988 | European Pat. Off. | |
| 2742464 | 3/1979 | Fed. Rep. of Germany | 623/22 |
| 3205526 | 9/1983 | Fed. Rep. of Germany | |
| 3341723 | 3/1985 | Fed. Rep. of Germany | |
| 8623855 | 11/1986 | Fed. Rep. of Germany | |
| 2578162 | 9/1986 | France | 623/22 |
| 2595241 | 9/1987 | France | 623/22 |

Primary Examiner—Richard J. Apley
Assistant Examiner—David J. Isabella
Attorney, Agent, or Firm—Kenyon & Kenyon

[57] ABSTRACT

The prosthetic acetabulum is formed of a metal shell structure of metal mesh and a plastic cup disposed in the shell structure. Both the shell structure and plastic cup have coincident meridian-disposed slots to permit the shell structure and cup to adapt to movements of the pelvis. The cup is also provided with a cavity for the femoral head which has spherical surface areas of different radii. The larger spherical surface area contains the slot and avoids locking of the femoral head during closing of the slot. A fixing tab is provided diametrically opposite the slot in the shell structure and is secured by bone screws to the edge of an undersurface of the pelvis.

12 Claims, 1 Drawing Sheet

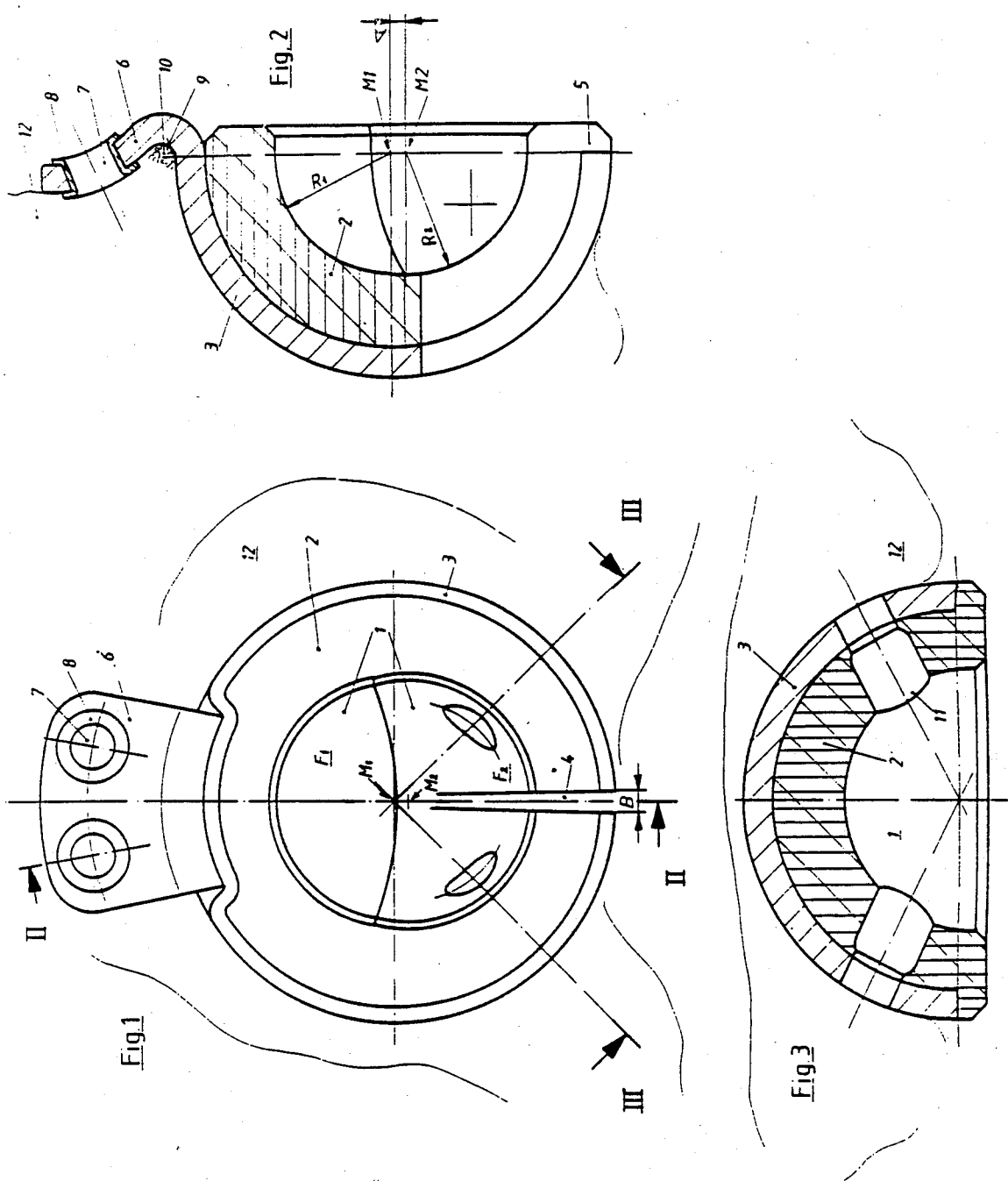

HEMISPHERICAL PROSTHETIC ACETABULUM

This invention relates to a hemispherical prosthetic acetabulum.

Heretofore, various types of structures have been employed for use as a prosthetic acetabulum. For example, European Patent Application No. 0265712 describes a two-part acetabulum which can be anchored by bone screws in a pelvis. German Pat. No. 3341723 and European Patent Application No. 0226762 describe hemispherical-like cups employing different radii for the outer surface or inner surface of the cup for implantation purposes. German OS No. 3205526 and French Patent No. 2595241 describe cup-shape metal structures employing tabs with apertures for the passage of bone screws for mounting in a pelvis.

Acetabula have also been known to be constructed in a resilient manner. For example, German Gebrauchsmuster No. 8623855 describes a two-part acetabulum employing a split outer shell for receiving a cup in a resilient manner. French Pat. No. 2426004 describes a two-part acetabulum having a slotted metal outer shell anchored in a plastic cup. In this case, the outer shell is formed with four slots which are distributed over the periphery and which extend in meridian directions. The function of these slots is to facilitate uniform spreading of the outer shell when the cup is pressed in so that a structure on the outer surface of the shell can penetrate in the spongiosa of a hip bone to fix the outer shell.

It has been found in practice that constructions, such as described in French Pat. No. 2426004, are often too rigid to be able to yield to resilient movements of the hip bone. This leads to relative "displacements" between the bone and the outer shell. Such displacements tend to cause irritation of the bone on one side and damage to the outer surface of the shell on the other side.

Accordingly, it is an object of the invention to provide a prosthetic acetabulum having a resilience very similar to the resilience of a pelvis.

It is another object to the invention to preclude irritation of a pelvic bone by a prosthetic acetabulum implanted therein.

It is another object of the invention to obviate damage to the outer surface of an acetabulum implanted in a pelvis.

Briefly, the invention provides a hemispherical prosthetic acetabulum which is comprised of a slotted metal shell structure and a slotted plastic cup.

The metal shell structure is of hemispherical shape and has a meridian-disposed elongated slot extending from an equatorial edge as well as a fixing tab extending diametrically opposite the slot for affixation to a pelvic bone. Further, the metal shell structure is made of metal mesh and is anchored in the plastic cup by being partially embedded in the plastic cup.

The plastic cup which is disposed in the shell structure has a meridian-disposed elongated slot coinciding with the slot in the shell structure and defines a cavity for receiving a femoral head. In addition, this cavity has a first spherical surface area of a radius corresponding to a radius of the femoral head with a center disposed on an equatorial plane of the cup as well as a second spherical surface area of the radius larger than the radius of the first area and a center disposed on the equatorial plane of the cup. The two centers are displaced from each other in a direction toward the slot in the cup.

The prosthetic acetabulum possesses an improved resilience as compared with previously known constructions since the cup is also formed with a meridian slot. In addition, the slots in both the cup and the shell structure extend at least substantially as far as the pole of the acetabulum. Further, since the maximum resilient compressibility of the shell structure corresponds to the width of the slot at the equatorial edge, the distance between the centers of the two radii of the spherical surface areas of the cup and the difference between the two radii each corresponds to one-half the width of the slot in the cup.

The "splitting" of the plastic cup as well as the shell structure requires additional steps in order to affix the acetabulum satisfactorily in a pelvis. To this end, the fixing tab is provided with suitable apertures for the passage of bone screws. In addition, the tab is disposed diametrically opposite the slot and is so aligned at implantation as to extend in the direction of the main loads on the acetabulum.

The risk of the femoral head locking when the pelvis or acetabulum experiences resilient deformations is obviated by the increased radius of the cup. Thus, as the plastic cup compresses so as to close the slot therein, the radius of the enlarged spherical surface area accommodates the femoral head without locking of the head.

The fixing tab on the shell structure is made so as to be permanently deformable intraoperatively. Thus, the tab can be adopted to individual pelvis shapes. Further, the tab may be deformed to define a fossa-like grove with the remainder of the shell structure in order to receive bone chips.

If necessary, the relatively resilient shell can be secured in the pelvis by means of bone screws which pass through a pair of apertures located on opposite sides of the slot of the shell structure. Likewise, the cup would be provided with a pair of apertures in alignment with the apertures in the shell structure.

These and other objects and advantages of the invention will become more apparent from the following detailed description taken in conjunction with the accompanying wherein:

FIG. 1 illustrates a plan view of an acetabulum constructed in accordance with the invention taken from the equator towards the pole;

FIG. 2 illustrates a view taken on line II—II of FIG. 1; and

FIG. 3 illustrates a view taken on line III—III of FIG. 1.

Referring to FIGS. 1 and 2, the hemispherical prosthetic acetabulum is comprised of a metal shell structure 3 and a plastic cup 2 which is disposed in the shell structure 3.

The metal shell structure 3 is made of a multi-layer metal mesh having at least one layer embedded in the plastic cup 2 for anchorage purposes. As indicated, the shell structure 3 has a meridian-disposed elongated slot 4 extending from an equatorial edge 5 (see FIG. 2) towards the pole. This slot has a width B, for example of approximately three millimeters, at the equatorial edge 5.

In addition, the shell structure 3 has a fixing tab 6 extending therefrom diametrically opposite the slot 4 for affixation to a pelvic bone 12. As indicated in FIG. 1, the fixing tab 6 is formed with two bores 7 through which bone screws (not shown) can extend and each of which is aligned with a metal sleeve 8. The function of the sleeves 8 is to protect the edge of the bores 7 from damage when the bone screws are being tightened and to ensure a definite position of the bone screws. The tab 7 is permanently deformable intraoperatively and may be bent into the shape shown in FIG. 2 so as to form a fossa-like grove 9 with the remainder of the shell structure 3 which can be filled with bone chips 10 during implantation.

The plastic cup 2 has a meridian-disposed elongated slot coinciding with the slot 4 in the shell structure 3 and defines a cavity 1 receiving a femoral head (not shown). The slot in the cup 2 extends in similar fashion to the slot 4 in the shell structure, substantially as far as the top, i.e. the pole of the cup 2.

The cavity 1 of the cup has two spherical surface areas $F_1$, $F_2$ each of a different radius from the other as well as centers $M_1$, $M_2$ which are offset from one another. The first spherical surface area $F_1$ is disposed within the portion of the cup 2 which is near the tab 6 and has a radius $R_1$ which corresponds to the radius of the femoral head (not shown) while the center $M_1$ is disposed on the equatorial plane of the cup 2. The other spherical surface area $F_2$ has a radius $R_2$ which is greater than radius $R_1$ while the center $M_2$ is offset from the center $M_1$ in the equatorial plane of the cup 2, being displaced from the center $M_1$ in a direction toward the slot in the cup. The difference between the first and second radii $R_1$, $R_2$ is equal to one-half the width B of the slot in the cup 2 at the equatorial edge 5. Likewise, the distance between the centers $M_1$, $M_2$ is equal to one-half of the width B of the slot in the cup 2 at the equatorial plane.

The two spherical surface areas $F_1$, $F_2$ will merge into each other so that a discrete edge line will exist between the two surfaces which will be evened during operation.

Referring to FIG. 3, the shell structure 3 has a pair of apertures for bone screws on opposite sides of the slot 4 while the cup 2 has a pair of apertures 11 aligned with the apertures in the shell structure for the passage of bone screws. These bone screws can be used to provide further fixation of the acetabulum in the pelvis 12.

As can be gathered from the pelvic bone 12 shown in diagramatic form, the acetabulum is so aligned at implantation that the tab 6 engages the undersurface of the pelvis and the slot 4 in the shell structure 3 as well as the slot in the cup 2, extends substantially in the direction of and within the incision made in the acetabulum. With this arrangement, the position and direction of the tab 6 substantially coincides with the direction of the main loading forces while the acetabulum portions on either side of the slot which have been additionally secured in the bone by bone screws can follow resilient deformations of the pelvis. Such deformations are mainly in the form of a narrowing and widening of the slot and of the incision in the acetabulum.

The larger "cavity" in the cup cavity 1 within the spherical surface area $F_2$ ensures that the femoral head (not shown) cannot become locked during these movements.

The invention thus provides a hemispherical prosthetic acetabulum which is able to follow displacements of the pelvis during use. Thus, relative displacements of the acetabulum and bone can be obviated. Also, the useful life of the acetabulum can be increased.

The invention also provides a prosthetic acetabulum having a surface near the bone which is of a resilience very similar to the resilience of the pelvis.

Further, the invention provides a prosthetic acetabulum which is of a soft and resilient construction capable of following resilient movements of the pelvis without any risk of the femoral head of a prosthetis becoming locked in place.

What is claimed is:

1. A hemispherical prosthetic acetabulum comprising
   a metal shell structure of hemispherical shape having a meridian-disposed elongated slot extending from a equatorial edge thereof and a fixing tab extending therefrom diametrically opposite said slot for affixation to a pelvic bone; and
   a plastic cup disposed in said shell structure, said cup having a meridian-disposed elongated slot coinciding with said slot in said shell structure and defining a cavity for receiving a femoral head, said cavity having a first spherical surface area of a first radius corresponding to a radius of a femoral head with a first center disposed on an equatorial plane of said cup and a second spherical surface area of a second radius larger than said first radius with a second center disposed on said equatorial plane of said cup, said second center being displaced from said first center in a direction toward said slot in said cup.

2. A hemispherical prosthetic acetabulum as set forth in claim 1 wherein said shell structure is made of metal mesh and is partially embedded in said plastic cup.

3. A hemispherical prosthetic acetabulum as set forth in claim 1 wherein the difference between said first and second radii is equal to one-half the width of said slot in said cup as measured at said equatorial edge of said shell.

4. A hemispherical prosthetic acetabulum as set forth in claim 1 wherein said tab is permanently deformable intraoperatively.

5. A hemispherical prosthetic acetabulum as set forth in claim 1 wherein said shell structure has a pair of apertures for bone screws on opposite sides of said slot thereof and said cup has a pair of apertures in alignment with said apertures in said shell structure.

6. A hemispherical prosthetic acetabulum as set forth in claim 1 wherein said tab extends from said shell structure to define a fossa-like groove therewith for receiving bone chips.

7. A hemispherical prosthetic acetabulum comprising
   a metal shell structure having a meridian disposed slot extending from an equatorial edge thereof; and
   a plastic cup disposed in said shell structure, said cup having a meridian-disposed elongated slot coinciding with said slot in said shell structure and defining a cavity for receiving a femoral head, said cavity having a first spherical surface area of a first radius corresponding to a radius of a femoral head with a first center disposed on an equatorial plane of said cup and a second spherical surface area of a second radius larger than said first radius with a second center disposed on said equatorial plane of said cup, said second center being displaced from said first center in a direction toward said slot in said cup.

8. A hemispherical prosthetic acetabulum as set forth in claim 7 wherein said centers are aligned coaxially with said slot.

9. A hemispherical prosthetic acetabulum as set forth in claim 8 wherein said shell structure is made of metal mesh and is partially embedded in said plastic cup.

10. A hemispherical prosthetic acetabulum as set forth in claim 8 wherein the difference between said first and second radii is equal to one-half the width of said slot in said cup as measured at said equatorial edge of said shell.

11. A hemispherical prosthetic acetabulum as set forth in claim 8 wherein said shell structure has a pair of apertures for bone screws on opposite sides of said slot thereof and said cup has a pair of apertures in alignment with said apertures in said shell structure.

12. A hemispherical prosthetic acetabulum as set forth in claim 8 wherein said slot in said cup extends to a pole of said cup.

* * * * *